United States Patent [19]

Foster

[11] 4,339,952

[45] Jul. 20, 1982

[54] CYLINDRICAL TRANSDUCER ULTRASONIC SCANNER

[75] Inventor: Francis S. Foster, Toronto, Canada

[73] Assignee: Ontario Cancer Institute, Toronto, Canada

[21] Appl. No.: 137,414

[22] Filed: Apr. 4, 1980

[30] Foreign Application Priority Data

Apr. 26, 1979 [CA] Canada ................................. 326460

[51] Int. Cl.$^3$ ............................................. G01N 29/04
[52] U.S. Cl. ...................................... 73/624; 128/660
[58] Field of Search ................. 73/624, 625, 626, 620, 73/627, 633, 641; 128/660

[56] References Cited

U.S. PATENT DOCUMENTS

| | | | |
|---|---|---|---|
| 3,881,466 | 5/1975 | Wilcox ................................... | 73/626 |
| 3,936,791 | 2/1976 | Kossoff .................................. | 73/626 |
| 3,953,825 | 4/1976 | Kino et al. ............................. | 73/626 |
| 3,954,098 | 5/1976 | Dick et al. ............................. | 73/621 |
| 3,971,962 | 7/1976 | Green .................................... | 73/641 |
| 4,028,934 | 6/1977 | Sollish .................................. | 73/620 |
| 4,058,003 | 11/1977 | Macovski ............................. | 73/626 |
| 4,072,289 | 2/1978 | Brueckner et al. ............. | 250/445 T |
| 4,103,677 | 8/1978 | Lansiart et al. ....................... | 73/621 |
| 4,117,446 | 9/1978 | Alais ..................................... | 73/626 |
| 4,121,468 | 10/1978 | Glover et al. ........................ | 73/626 |
| 4,258,574 | 3/1981 | Hildebrand et al. ................ | 73/625 |

OTHER PUBLICATIONS

C. B. Burckhardt et al., "Ultrasound Axicon: Device for Focussing Over Large Depth", *Journal Acoustical Society of America*, vol. 54, No. 6, pp. 1628–1630, 1973.

D. R. Dietz et al., "Expanding Aperture Annular Array", *Ultrasonic Imaging*, vol. 1, No. 1, pp. 56–75, 1979.

*Primary Examiner*—Stephen A. Kreitman
*Attorney, Agent, or Firm*—Watts, Hoffmann, Fisher & Heinke Co.

[57] ABSTRACT

An ultrasonic image of improved resolution is obtained by utilizing separate transducers for transmission and reception of ultrasonic pulses utilized for imaging, one transducer being a cylindrical or simulated cylindrical transducer having a line focus and the other transducer being aimed along the focus of the first transducer. An area to be imaged may be scanned by rotating and/or traversing the transducers as a unit.

21 Claims, 6 Drawing Figures

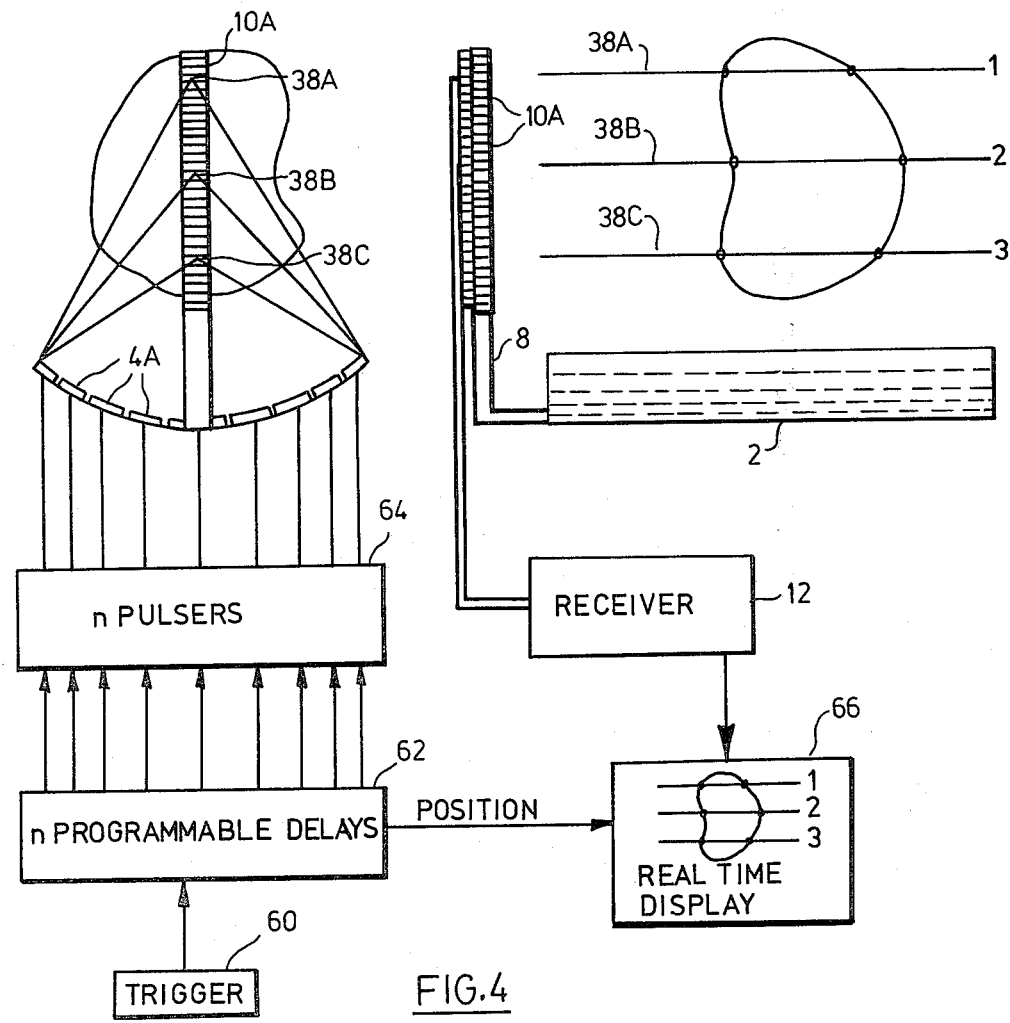

CYLINDRICAL TRANSDUCER ULTRASONIC SCANNER

BACKGROUND OF THE INVENTION

1. Field of the Invention

This invention relates to ultrasound imaging systems.

2. Description of the Prior Art

Ultrasound imaging systems are attractive for medical applications because they permit imaging of internal structures of the body without the use of harmful forms of radiation. Numerous proposals have been made for such systems and many are in actual use. Although the systems vary widely in detail, most known systems basically utilize an ultrasonic transducer or bank of transducers to beam pulses of ultrasound into a structure to be imaged and to receive reflections of those pulses. The beamed pulses are directed through the structure to be imaged in a suitable scanning pattern by mechanical and/or electronic means.

A major problem with such systems is lack of resolution in lateral directions. Some improvement can be obtained utilizing large aperture transducers which are electronically or acoustically focused but this improvement is at the expense of a very shallow depth of field. Consequently sophisticated means are required to maintain focus throughout a scan, and the operation of such means tends to limit the rate of scan and thus increase the time taken to generate an image. Even with such means, resolution is often inadequate for reliable detection of small anomalies in the structure being imaged.

An example of a known type of B-scanning ultrasonic system is disclosed in U.S. Pat. No. 4,014,207, issued Mar. 29, 1977, to Meyer, et al., for SECTOR SCANNING ULTRASONIC INSPECTION APPARATUS.

SUMMARY OF THE INVENTION

I have now found that excellent lateral resolution can be maintained over a substantial depth of field by utilizing separate transducers for transmission and reception of ultrasound pulses utilized for imaging a structure, one transducer being an actual or simulated cylindrical or part-cylindrical transducer having a line focus, and the other being aimed along said line focus of the said one transducer. The line of focus is moved relative to the structure being imaged so as to provide a desired scan of the latter.

The invention is described further with reference to the exemplary embodiments shown in the accompanying drawings, in which:

DESCRIPTION OF THE DRAWINGS

FIGS. 2A and 3A are diagrams illustrating how the apparatus of FIG. 1 can be utilized in two different modes to scan a breast;

FIGS. 2B and 3B illustrate the types of image plot obtained in the two modes; and FIG. 4 schematically illustrates a modified embodiment of the invention which can be scanned electronically in a vertical plane.

DESCRIPTION OF THE PREFERRED EMBODIMENT

Figure 1:
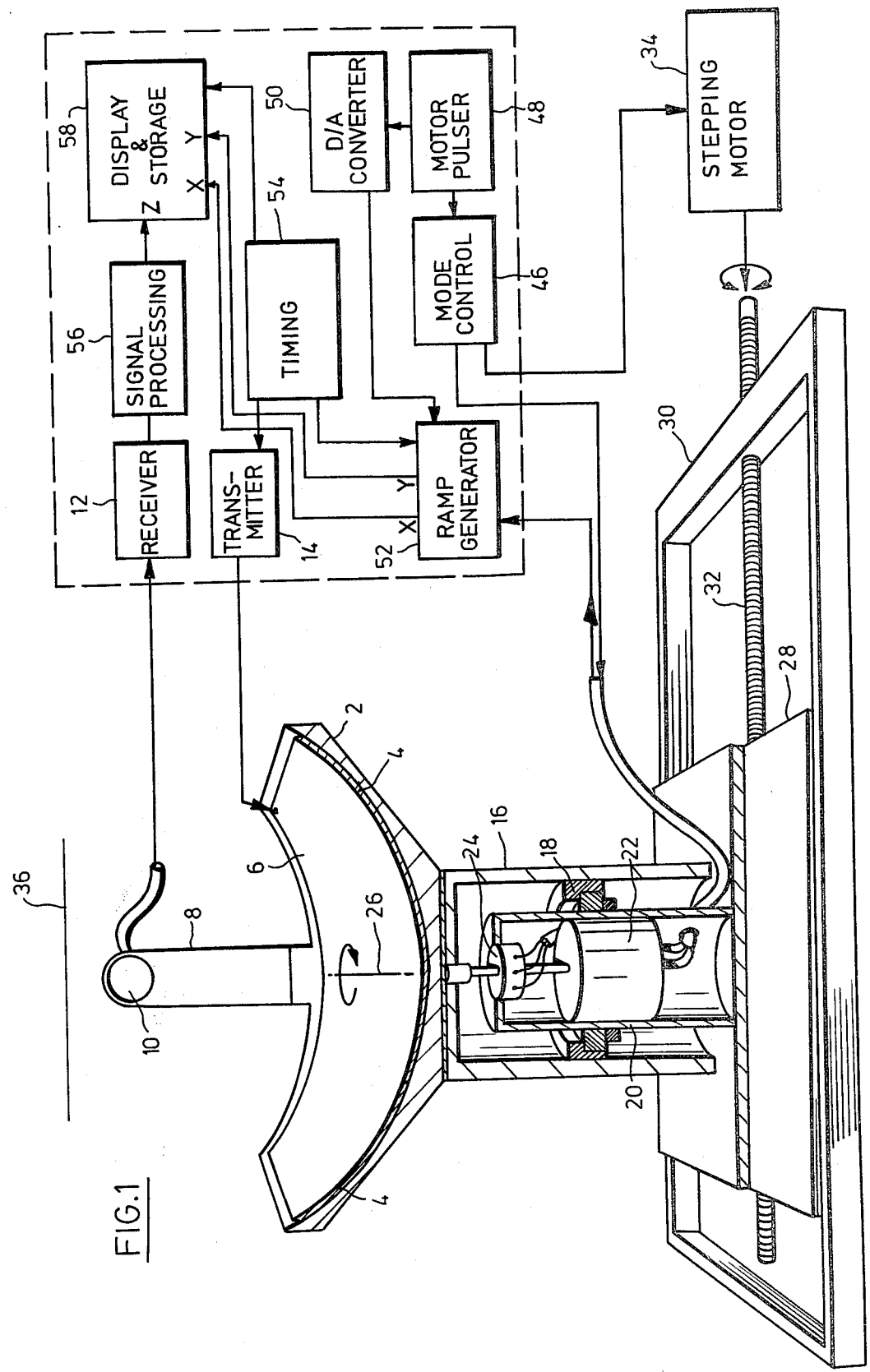
FIG. 1 is a diagrammatic part sectional, part schematic drawing of one embodiment of the invention, intended for breast scanning.

Referring to FIG. 1, an aluminum trough 2 has, bonded to its surface by means of an epoxy resin, a sheet 4 of piezoelectric synthetic plastic, in this instance polyvinylidene fluoride sheet, thirty microns in thickness, available from Kreha Corp., of New York, USA. The aluminum trough 2 acts as a back electrode whilst the upper surface of the plastic 4 is metallized to form a front electrode of the part cylindrical transducer formed by the trough. The characteristics of such a transducer are well suited to 1-10 MHz frequencies commonly employed in medical ultrasound imaging. The transducer trough 2 has a radius of 14.0 cm, a length of 20 cm, and subtends an angle of 120°.

A pillar 8 mounted at one end of the trough carries a second transducer 10, which may be a conventional disc transducer capable of operating at the desired operating frequency. It need not be highly directional although it should be aligned with the axis of the trough 2, which is also the focus of the transducer formed by the sheet 4. The transducer 10 is connected to a receiver 12, whilst the transducer formed by a sheet 4 is energized by high frequency pulses gated from a transmitter 14 generating an energizing potential at, typically, 3-5 MHz at 10-200 volts peak to peak.

The trough 2 is mounted on a housing 16 supported by a fluid-tight bearing assembly 18 of an inner housing 20 which contains a stepping motor 22 and a sine-cosine potentiometer 24. The motor is operative to rotate the trough 2 about the axis 26, while the potentiometer 24 signals its angular position.

The inner housing 20 is supported by a platform 28 which can be moved laterally in a frame 30 by means of a drive screw 32 which can be rotated by a further stepping motor 34. Further hydraulic or screw operated means (not shown) may be provided to lift or lower the frame 30 bodily within a tank of water (not shown) in which the assembly is submerged to a depth such that the level 36 of the water is above the transducer 10. The water forms an ultrasonic coupling medium between a patient's breast to be imaged and the transducers 4 and 10. A thin plastic membrane may be provided to protect the patient from direct contact with the water and a suitable supporting couch (not shown) is of course provided to enable the patient to assume a suitable position relative to the apparatus, in accordance with known practice for ultrasonic breast imaging systems.

The apparatus is capable of operation in two different scanning modes. In a first mode, as illustrated in FIGS. 2A and 2B, the motor 22 is utilized to rotate the trough 2 and thus the line of focus 38 of the transducer 4 about the axis 26, so that the line 38 intersects a breast 40 being examined diametrically at successive angularly incremented locations 42 as the trough is stepped by motor 22, as shown in FIG. 2B. In the second mode, the line of focus intersects the breast 40 at successive locations 44 laterally displaced by motor 34 and in a common plane as shown in FIG. 3B. A mode control 46 determines which motor 22 or 34 is stepped by a motor pulser 48. The motor pulser 48 also applies pulses to a digital-/analog converter 50 whose output is applied to a time base unit 52 comprising X and Y ramp generators. The time base unit also receives an input from a timing unit 54 which applies gating pulses to the transmitter 14. When the apparatus is operating in the second mode, the output from the D/A converter 50 is processed by the time base unit 52 to provide an X signal proportional to the lateral displacement of the platform 28. The input from the timing unit is utilized to generate a sawtooth waveform generating a Y-scan at the repetition rate of the pulses applied to the transmitter, but subject to a delay such that the scan coincides with the reception by receiver 12 of signals from the transducer 4 scattered by a breast being imaged and picked up by the transducer 10. The signals from the receiver 12 are processed in a signal processing unit 56, in which they may be subjected to known noise reduction and signal enhancement techniques. The processed signals are applied to a display and storage unit, for example a storage oscilloscope in which the beam is Z-modulated by the received signal and deflected on the X and Y axes to provide an image of the type shown in FIG. 3B.

In the first mode, operation is similar except that the inputs to the time base from the sine-cosine potentiometer 24 and the timing unit 54 are combined to provide X and Y outputs giving a vectorscope type display similar to that shown in FIG. 2B.

In operation, the time unit 54 gates short pulses of high frequency electrical energy from the transmitter 14 to the transducer 4 in which it is converted into a cylindrical wavefront of ultrasound which converges to a sharp focus on the line 38. Scattering of the ultrasound pulse takes place in the breast being imaged, the degree of scattering being dependent on the nature of the tissue causing the scattering. Most of this scattering will occur along the line of focus and components aligned with the line of focus will be picked up by the transducer 10 after a time delay dependent on the distance travelled by the scattered sound energy. Since ultrasound intensity on the line 38 will be very high compared with that elsewhere within the pickup range of the transducer 10, the signals received by that transducer will represent successive soundings along the line of focus as it is scanned through a plane intersecting the tissue being examined. It is found that the resolution and depth of field obtained are substantially better than with conventional techniques when operating at similar frequencies and imaging rates. Typical conditions of operation utilize an ultrasound pulse length of 1 microsecond at a frequency of 3 MHz and a pulse repetition rate of 1 kHz.

In the embodiment so far described, scanning is achieved solely mechanically. However, by utilizing a cylindrical transducer or simulated cylindrical transducer having an electronically variable line of focus, together with a second transducer or set of transducers of sufficient extent to receive ultrasound energy scattered along said line of focus throughout its range of movement, an electronic scan is achieved.

This is illustrated in FIG. 4, in which the film 4 of FIG. 1 is replaced by a series of n parallel strips of film 4A. The transducer 10 is replaced by a line of transducers 10A connected to the receiver 12, preferably with some means to exclude output from transducers 10A which at any particular stage in the scan are not in line with the focus 38. The line of focus 38 of the cylindrical transducer can be varied as shown at 38A, B and C in known manner by pulsing the strips 4A independently. Trigger pulses are derived from a trigger 60 fed through a series of n electronically variable delay lines 62, conveniently implemented by "bucket brigade" charge coupled devices, and these trigger pulses are used to drive n pulsers 64 driving the individual strips 4A to produce ultrasound pulsers. By relatively increasing or decreasing the delay applied to the outer strips as compared to the inner strips, the position of the line of focus can be varied, and by varying the line of focus progressively as pulsing of the strips continues, a scan can be achieved. The signal used to control the delay lines can also be used to provide the Y signal of a display 66, the X signal being derived from trigger pulses from the trigger 60. This electronic scan in one plane can be combined with a mechanical scan in an orthogonal plane to provide three-dimensional imaging of a tissue structure to be examined.

The function of the delay lines 62 is to equalize the combined electrical and acoustic delays occurring between the generation of pulses by the trigger 60, and the arrival of the ultrasound pulses, at the desired line of focus 38. It will thus be appreciated that a similar delay line arrangement can be used between the strips 4A and the receiver 12 if the cylindrical transducer is utilized to receive ultrasound scattered from pulses transmitted by the transducers 10A.

It will be understood that the above embodiments of the invention are described by way of example only. Many variations are possible.

The functions of the cylindrical transducer, and the transducer aligned with the line of focus of the cylindrical transducer may be transposed, so that the latter becomes the transmitting transducer and the former the receiving transducer. The mode chosen is largely a matter of convenience in design and electrical matching.

The cylindrical transducer itself is subject to a wide range of constructional variation. Thus in the embodiment of FIG. 4, the strips 4A could be arranged in a common plane, focussing being achieved entirely by the electronic means described. Focussing of the output of a plane transducer or battery of transducers could also be achieved by use of an acoustic lens so as to simulate a cylindrical transducer.

Whilst in the embodiments described the cylindrical transducer has subtended an effective angle of about 120° at its focus, this angle can of course be varied. However, if the angle is reduced substantially below about 120°, the definition of the image achieved also deteriorates substantially. Further increases in the angle substended provide relatively little improvement in image sharpness, whilst making it more difficult to bring a structure to be imaged into an appropriate positional relationship with the transducers.

The piezoelectric plastic film utilized in the exemplary embodiments of the invention has particularly convenient characteristics for this application, but there is of course no reason why other ultrasonic transducer materials, capable of being incorporated into a functional actual or simulated cylindrical transducer, should not be used.

The embodiments described show a transducer 10 or 10A at one end only of the line of focus 38. In some cases, improved results will be obtained by providing transducers at both ends of the line of focus 38, and suitably combining the signals obtained into the final display.

It will also be understood that the invention fundamentally resides in the arrangement of transducers utilized, and that a wide range of possibilities exists as to the means utilized to scan the line focus of the cylindrical transducer through the structure to be imaged, and to construct an image from the signals received.

I claim:

1. An ultrasonic imaging device, comprising transducer means for transmitting ultrasound pulses into a structure to be imaged and receiving ultrasound scattered by said structure and generating signals in response thereto, means to energize said transducer means to transmit said pulses, scanning means for progressively relating said transducer means to successive linear portions of said structure according to a scanning pattern, and receiver and signal processing means for assembling an image from said generated signals, wherein the transducer means comprises separate transmitting and receiving transducers, one of said transducers being a real or simulated cylindrical transducer having a line focus successively coincident with the axes of said linear structure portions, and the other of said transducers being in coaxial alignment with and aimed along said line focus, the scanning means being operative to move said line focus in relation to the structure to be imaged in accordance with said scanning pattern.

2. An imaging device according to claim 1, wherein the cylindrical transducer is the transmitting transducer.

3. An imaging device according to claim 1, wherein the cylindrical transducer is mounted on a trough shaped support, and the other transducer is supported from the trough in alignment with the cylindrical axis of a cylindrical transducer to form the transducer assembly.

4. An imaging device according to claim 3, wherein the cylindrical transducer is formed by a sheet of piezoelectric synthetic plastic film.

5. An imaging device according to claim 3, wherein the scanning means includes apparatus for bodily translating the transducer assembly so as to move the focus of the cylindrical transducer in a plane intersecting a structure to be imaged.

6. An imaging device according to claim 3, wherein the scanning means includes apparatus for bodily rotating the transducer assembly so as to move the focus of the cylindrical transducer in a plane intersecting a structure to be imaged.

7. An imaging device according to claim 5 or 6, further including means for bodily translating the transducer assembly in a direction perpendicular to said plane intersecting a structure to be imaged whereby to image successive layers therein.

8. An imaging device according to claim 1, further comprising focussing means associated with said cylindrical transducer for electronically changing the position of said line of focus through a range of locations, said other transducer of said transducer assembly being configured to remain in alignment with said line of focus throughout said range of positions.

9. An imaging device according to claim 8, wherein said focussing means is controlled by said scanning means so as to move the position of the line of focus in accordance with said scanning pattern.

10. An imaging device according to claim 8 or 9, wherein the cylindrical transducer comprises a plurality of elements extending parallel to said line of focus, and each associated with electronically variable delay means operable to equalize the combined electrical and acoustic transmission or reception delays between the energizing or signal processing means and the desired line of focus.

11. An ultrasonic examination system comprising:

(a) a first transducer dedicated exclusively for transmitting ultrasonic energy focused in a line focus configuration from a direction transverse to the line focus;

(b) circuitry for actuating the first transducer to transmit the ultrasonic energy;

(c) a second transducer dedicated exclusively for receiving ultrasonic energy, said second transducer being axially aligned with the line focus;

(d) imaging circuitry for processing signals produced by the receiving transducer, and (e) a display system responsive to the processed signals for producing an image of internal structure of a subject into which the line focus extends.

12. The system of claim 11, further comprising:
scanning means for moving the transducers relative to the subject for effecting an ultrasonic B-scan.

13. The system of claim 11, wherein said receiving transducer has a substantially disc shape and a substantially flat ultrasonic energy receiving surface.

14. An ultrasonic examination system comprising:

(a) a first transducer dedicated exclusively to transmitting ultrasonic energy into a subject along a line focus with which the first transducer is axially aligned;

(b) circuitry for electrically actuating the first transducer to produce the ultrasonic energy along a line directed into a subject;

(c) a second transducer dedicated exclusively to receiving ultrasonic energy from the line focus from a direction transverse to the line focus;

(d) imaging circuitry coupled to the receiving transducer for processing signals produced by the receiving transducer in response to receipt of the scattered ultrasonic energy, and (e) a display system responsive to the processed signals to produce an image of internal structure of the subject.

15. A method of ultrasonic examination, comprising the steps of:

(a) directing ultrasonic energy to a line focus within a subject from a direction transverse to the line focus;

(b) receiving ultrasonic energy scattered within the subject from a direction substantially axially aligned with the line focus;

(c) producing electrical signals representing the received ultrasonic energy, and (d) processing the electrical signals to produce an image representation of internal subject structure.

16. An ultrasonic imaging method comprising the steps of:

(a) directing ultrasonic energy along a line focus extending into a subject from a direction axially aligned with the line focus;

(b) receiving ultrasonic energy scattered from within the subject from a direction transverse to the line focus;

(c) converting the received ultrasonic energy to electrical signals, and (d) processing the electrical signals to produce an image representation of internal subject structure.

17. An ultrasonic examination system comprising:

(a) a first transducer for transmitting ultrasonic energy substantially focused in a line focus configuration from locations spaced from the line focus:

(b) circuitry for actuating the first transducer to transmit ultrasonic energy;

(c) a second transducer dedicated exclusively for receiving ultrasonic energy, said second transducer being axially aligned with the line focus;
(d) imaging circuitry for processing signals produced by the receiving transducer, and
(e) a display system responsive to the processed signals for producing an image of internal structure of a subject into which the line focus extends.

18. An ultrasonic examination system comprising:
(a) a first transducer for transmitting ultrasonic energy substantially focused in a line focus configuration from a direction laterally spaced from the line focus;
(b) circuitry for actuating the first transducer to transmit ultrasonic energy;
(c) a second transducer dedicated exclusively for receiving ultrasonic energy, said second transducer being axially aligned with the line focus;
(d) imaging circuitry for processing signals produced by the receiving transducer, and
(e) a display system responsive to the processed signals for producing an image of internal structure of a subject into which the line focus extends.

19. An ultrasonic examination system comprising:
(a) a first transducer for transmitting ultrasonic energy substantially focused in a line focus configuration from an extended surface substantially laterally displaced from the line focus;
(b) circuitry for actuating the first transducer to transmit ultrasonic energy;
(c) a second transducer dedicated exclusively for receiving ultrasonic energy, said second transducer being axially aligned with the line focus;
(d) imaging circuitry for processing signals produced by the receiving transducer, and
(e) a display system responsive to the processed signals for producing an image of internal structure of a subject into which the line focus extends.

20. An ultrasonic examination system, comprising transducer means for transmitting ultrasound pulses into a linear portion of a structure to be examined and for receiving ultrasound scattered by said structure portion and generating signals in response thereto, means to energize said transducer means to transmit said pulses, and means for displaying said generated signals, wherein the transducer means comprises separate transmitting and receiving transducers, one of said transducers being spaced from the axis of said structure portion but having a line focus coincident with said axis, and the other of said transducers being aligned with and aimed along said axis.

21. An ultrasonic examination method comprising transmitting ultrasound pulse from one transducer and receiving ultrasound scattered by a structure being examined at a second transducer to provide a signal for display, one of said transducers having a line focus in said structure from a lateral direction and the other being aligned with and aimed along said line focus.

* * * * *